US00PP28270P3

(12) United States Plant Patent
Sheehan

(10) Patent No.: US PP28,270 P3
(45) Date of Patent: Aug. 15, 2017

(54) GRAPEVINE 'SHEEGENE-17'

(50) Latin Name: *Vitis vinifera*
Varietal Denomination: Sheegene-17

(75) Inventor: Timothy P. Sheehan, Vancouver, WA (US)

(73) Assignee: Sheehan Genetics, LLC, Fresno, CA (US)

( * ) Notice: Subject to any disclaimer, the term of this patent is extended or adjusted under 35 U.S.C. 154(b) by 776 days.

(21) Appl. No.: 13/506,354

(22) Filed: Apr. 12, 2012

(65) Prior Publication Data

US 2013/0276181 P1 Oct. 17, 2013

(51) Int. Cl.
*A01H 5/08* (2006.01)

(52) U.S. Cl.
USPC ..... Plt./207
CPC ..... *A01H 5/0812* (2013.01)

(58) Field of Classification Search
USPC ..... Plt./205, 207
See application file for complete search history.

(56) References Cited

U.S. PATENT DOCUMENTS

PP24,316 P3 * 3/2014 Dulcich et al. ..... Plt./207
2013/0198918 P1 8/2013 Dulcich

OTHER PUBLICATIONS

Xu et al., Proc. Fla. State Hort. Soc. 118:260-262. 2005.*
Sharathchandra et al., PLoS One. 2011; 6(2): e14708, 2011, 30 pages.*
Park et al, Regeneration of Grape (*Vitis labruscana* cv. Kyoho) by Shoot-Tip Culture, Journal of Plant Biology, Dec. 2001, 44(4):185-192.*

* cited by examiner

*Primary Examiner* — Anne Grunberg
(74) *Attorney, Agent, or Firm* — Dentons US LLP

(57) ABSTRACT

A new and distinct variety of grapevine characterized by the production of medium, green-colored seedless grapes that mature in late August when grown in the San Joaquin Valley of Central California. The grapes of this new variety are produced on strong woody stems and branches and are well adapted to commercial handling.

1 Drawing Sheet

Latin name of the genius and species of the plant claimed: The claimed plant relates to a new and distinct variety of *Vitis vinifera* to be known as 'Sheegene-17'.

CROSS REFERENCE TO RELATED APPLICATIONS

The claimed plant is not subject of a related application.

STATEMENT OF ANY FEDERALLY-SPONSORED RESEARCH AND DEVELOPMENT

The claimed plant is not subject of Federally-sponsored research or development.

VARIETY DENOMINATION

The new variety of *Vitis vinifera* is the result of hybridization of 'Princess' (unpatented), the pollen parent, and 'Red Globe' (U.S. Plant Pat. No. 4,787), the seed parent. The new variety was first hybridized by Timothy P. Sheehan in the Spring of 2000. The new variety was asexually propaged in the dormant season of 2003, grafted on virus-free rootstock in a *Vitis vinifera* variety block located East of Fowler, Calif. The new variety was planted as rooted cuttings in the dormant season of 2006 in a *Vitis vinifera* variety block located several miles South of McFarland, Calif. The new variety produces a medium, green-colored seedless grape with a sweet flavor. The new variety has been shown to maintain its distinguishing characteristics through asexual propagation.

The new variety is distinguished from its pollen parent, 'Princess' (unpatented), in that the new variety produces green-colored seedless grapes, as compared to the white-colored seedless grapes produced by its pollen parent, 'Princess' (unpatented). The new variety is distinguished from its seed parent, 'Red Globe' (U.S. Plant Pat. No. 4,787), in that the new variety produces medium sized green-colored seedless grapes, as compared to its seed parent, 'Red Globe' (U.S. Plant Pat. No. 4,787), that produces exceptionally large red-colored seeded grapes.

BACKGROUND OF THE INVENTION

The present invention relates to a new and distinct variety of grapevine that produces a medium, green-colored seedless grape that matures in late August when grown in the San Joaquin Valley of Central California.

SUMMARY OF THE INVENTION

The 'Sheegene-17' grapevine is characterized by producing a medium, green-colored seedless grape that has a sweet flavor and it is productive and mature for harvesting and shipment in late August when grown in the San Joaquin Valley of Central California. The new variety can be compared to 'Thompson Seedless' (unpatented) but the grapes produced by the new variety are larger and mature two to three weeks later, among other distinguishing characteristics.

BRIEF DESCRIPTION OF THE DRAWINGS

The accompanying drawing is a color photograph of the new variety of grapevine displaying leaves, tendrils, shoots, mature grapes, late berry cluster, mature berry cluster, and four grapes cut in half.

Across the top portion of the photograph is a late berry cluster with a young shoot to the right of the cluster.

Directly below the cluster and to the left is an immature shoot with leaves.

At the center of the photograph is a mature berry cluster with a mature cane and nodes to the right of the cluster.

Just below the mature berry cluster are four grapes cut longitudinally and horizontally displaying the heart and pulp.

Below the cut grapes are leaves displaying the upper and lower surfaces.

DETAILED BOTANICAL DESCRIPTION

Referring more to the horticultural description of the new and distinct variety of grapevine, the following has been observed under the ecological conditions prevailing at the origin vineyard located near McFarland, Calif., in the San Joaquin Valley of Central California. All major color descriptions are by reference to the Dictionary of Color by Maerz & Paul, First Edition, published in 1930. Common colors names are also used in several instances.

Vine:

*Size*.—Medium for a seven year-old vine.
*Vigor*.—Very good.
*Chilling requirements*.—Normal for grapevines in the lower San Joaquin Valley of Central California.
*Productive capacity*.—Very good.
*Regularity of bearing*.—Regular.

Trunk:

*Size*.—Medium; 8 inches [20.32 cm] in circumference, 15 inches [38.10 cm] above ground (5 year old wood).
*Surface texture*.—Rough and shaggy.
*Color of bark*.—P1.3 G9 Kaffa Hampshire Brown (5 year old wood).
*Mature cane color*.—P1.7 L8 Mauve Taupe Copra (8 to 12 month old wood).
*Nodes*.—Four on cane.
*Length between nodes*.—4 inches [10.16 cm].
*Shoot length*.—6 to 6.5 inches [15.24 to 16.51 cm].
*Shoot habit*.—Droopy.
*Tendrils number/location*.—Single at node.
*Tendrils length*.—1.5 to 3.75 inches [3.81 to 9.53 cm].
*Tendrils locale*.—At nodes.
*Tendrils form*.—Bifurcate.
*Tendrils texture*.—Firm.
*Bud shape*.—Convex.
*Bud size*.—0.24 to 0.28 inches [6 to 7 mm] wide; 0.24 to 0.28 inches [6 to 7 mm] long.
*Bud fruitfulness*.—Very good.

Branches:

*Size*.—Medium.
*Cordons*.—26.5 inches [67.31 cm] on one side of trunk; 30.0 inches [76.20 cm] on the other side of trunk.
*Surface texture*.—Slightly rough.
*Color* (*one year or older branches*).—P1.6 K9 Havana Rose.
*Color* (*immature branches*).—P1.19 K6 Piquant gr.

Leaves:

*Size*.—Medium.
*Density*.—Dense.
*Average length*.—3.75 to 5.25 inches [9.53 to 13.34 cm].
*Average width*.—5.00 to 6.5 inches [12.70 to 16.51 cm].
*Form*.—Pentagonal.
*Texture* (*upper surface*).—Smooth.
*Texture* (*lower surface*).—Slightly rough.
*Color* (*upwardly disposed surface*).—P1.23 J8 Mt. Vernon gr.
*Color* (*downwardly disposed surface*).—P1.21 K8 Teak fern.
*Color* (*leaf vein*).—P1.17 L3 Endive.
*Marginal form*.—Toothed.
*Leaf margin*.—Slightly undulate.
*Leaf vein thickness*.—0.08 inches [2 mm].
*Stem glands*.—None.
*Petiole size*.—Moderate.
*Petiole length*.—2.75 to 5.25 inches [6.99 to 13.34 cm].
*Petiole thickness*.—0.12 inches [3 mm].
*Petiole color*.—P1.6 L8 Dark Cardinal Rose Lustre.
*Stem glands*.—None.
*Stipules*.—None.
*Lobes* (*average*).—Five.
*Stipules*.—None.
*Tooth size*.—0.31 to 0.39 inches [8 to 10 mm] in width; 0.31 inches [8 mm] in length.
*Tooth number*.—7 to 14 per lobe.
*Tooth shape*.—Convex.

Inflorescence:

*Size*.—8.00 to 9.00 inches [20.32 to 22.86 cm] in length.
*Number borne per spur*.—Two.
*Number borne per vine*.—Thirty.

Flowers:

*Flower buds* (*size*).—Small.
*Flower buds* (*surface*).—Glabrous.
*Flower buds* (*quantity*).—Moderate.
*Date of bloom*.—Apr. 15, 2007.
*Date of full bloom*.—Apr. 21, 2007.
*Size of bloom*.—0.20 to 0.24 inches [5 to 6 mm].
*Calyptra* (*flower cap*) color.—P1.19 D2 Reed.
*Berry color*.—P1.18 E6 Oriental Tiber gr.
*Petals size*.—0.08 to 0.12 inches [2 to 3 mm].
*Stamen* (*anther*) *color*.—P1.17 B1 cream color to yellowish brown.
*Date of first visible berries*.—May 1, 2007.

Fruit:

*Solids*.—16.9 Brix.
*Acids*.—0.61.
*Sugar/acid ratio*.—27.7.
*Juice pH*.—3.51.
*Seeds*.—None.
*Rudimentary seed structures*.—One to two.
*Capstem pedicel*.—0.24 to 0.39 inches [6 to 10 mm].
*Berry weight*.—5.68 grams (0.20 oz).
*Cluster size*.—Medium.
*Cluster average length* (*not including stem*).—10 inches [25.40 cm].
*Cluster average diameter*.—6.25 inches [15.88 cm].
*Cluster average weight*.—965.6 grams (34.06 oz).

*Cluster density*.—Compact.
*Cluster form*.—Conical.
*Stem* (*length*).—1.5 inches (3.81 cm).
*Stem caliper*.—0.28 inches [7 mm].
*Berry size*.—Medium.
*Berry form*.—Ovate.
*Berry numbers* (*average*).—Approximately 166 berries per bunch.
*Berry size* (*average dimension along longitudinal axis*).—0.91 to 1.14 inches [26 to 29 mm].
*Berry size* (*average dimension along transverse axis*).—0.83 to 0.91 inches [21 to 23 mm].

Skin:
*Skin thickness*.—Medium.
*Texture*.—Semi-tough.
*Tendency to crack*.—Slight.
*Ground color*.—P1.19 C6 Pistachio gr. Pistache.
*Pulp color*.—P1.19 C6 Pistachio gr.
*Lenticels*.—None.

Flesh:
*Flesh color*.—From P1.19 C16 Pistachio gr. Pistache.
*Juice production*.—Moderate.
*Flavor*.—Very good.
*Aroma*.—Very mild.
*Texture*.—Firm.
*Ripening*.—Even.
*Eating quality*.—Very good.
*Use*.—Fresh market .
*Keeping quality*.—Good.
*Resistance to disease*.—Unknown.
*Harvesting*.—Late August in the San Joaquin Valley of Central California.
*Shipping and handling qualities*.—Very good.

The invention claimed is:

1. A new and distinct variety of grapevine substantially as described and illustrated herein, characterized principally by its production of medium, green-colored seedless grapes that mature two to three weeks later than 'Thompson Seedless' (unpatented) which is somewhat resembles.

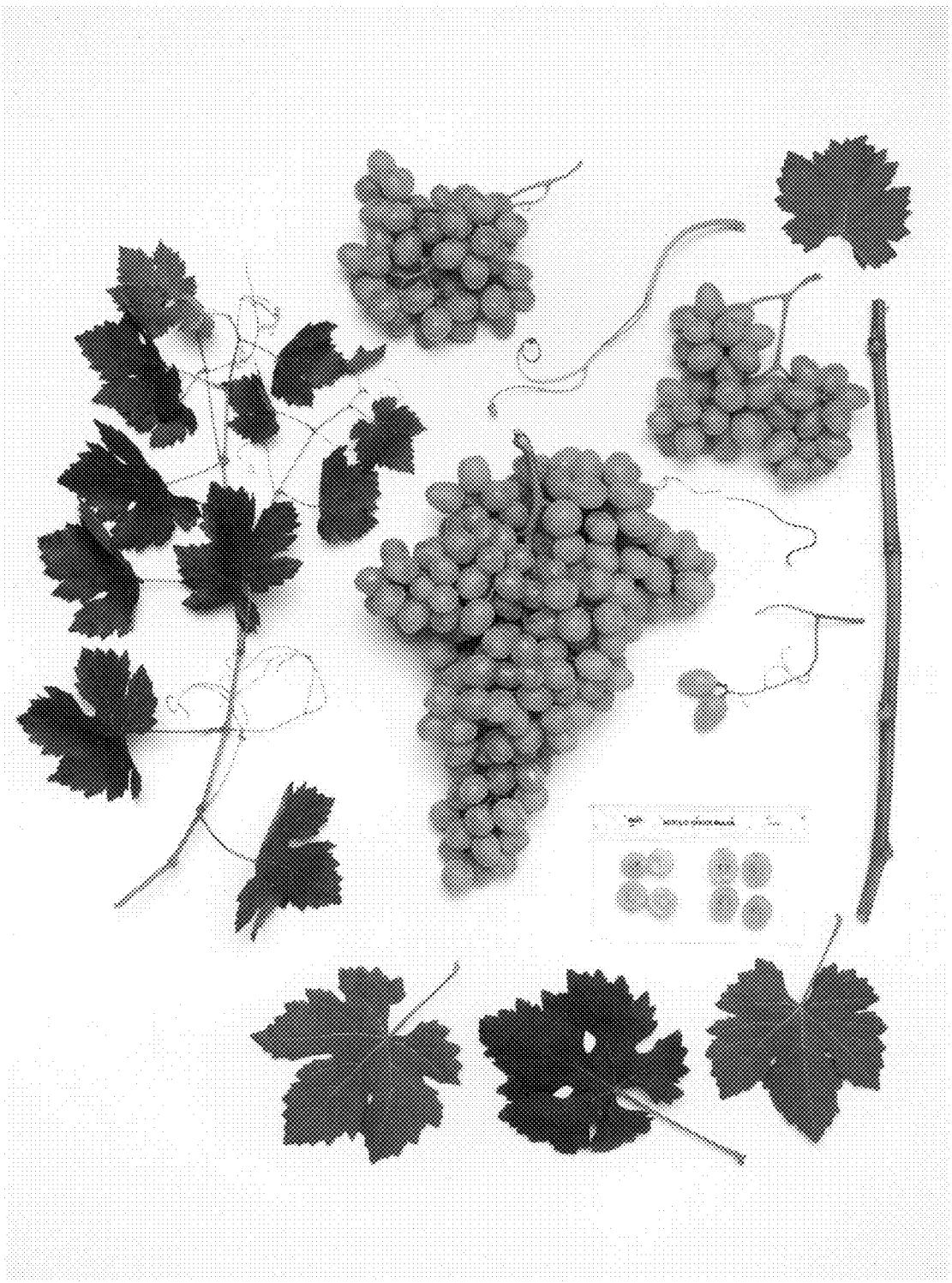

* * * * *